United States Patent [19]

Solomon et al.

[11] Patent Number: 5,181,514
[45] Date of Patent: Jan. 26, 1993

[54] TRANSDUCER POSITIONING SYSTEM

[75] Inventors: Rodney J. Solomon, Needham; Martin K. Mason, Andover, both of Mass.; George Gruner, Everett, Wash.; James T. Fearnside, Lexington, Mass.

[73] Assignee: Hewlett-Packard Company, Palo Alto, Calif.

[21] Appl. No.: 703,648

[22] Filed: May 21, 1991

[51] Int. Cl.$^5$ ................................ A61B 8/00
[52] U.S. Cl. .................... 128/660.09; 128/660.08; 128/661.01; 128/4; 128/662.06
[58] Field of Search ............... 128/660.08, 660.01, 128/660.09, 660.10, 662.03, 662.06, 4, 661.01

[56] References Cited

U.S. PATENT DOCUMENTS

| | | | |
|---|---|---|---|
| 3,744,479 | 7/1973 | Stein et al. | 128/661.04 |
| 4,375,818 | 3/1983 | Suwaki et al. | 128/4 |
| 4,543,960 | 10/1985 | Haru et al. | 128/662.06 |
| 4,593,314 | 6/1986 | Siler | 128/661.04 |
| 4,735,211 | 4/1988 | Takasugi | 128/661.04 |
| 4,841,979 | 6/1989 | Dow et al. | 128/660.10 |
| 4,869,257 | 9/1989 | Molnar et al. | 128/660.10 |
| 4,880,009 | 11/1989 | Yanagawa | 128/660.09 |
| 4,928,699 | 5/1990 | Sasai | 128/662.06 |
| 4,982,724 | 1/1991 | Saito et al. | 128/4 |

OTHER PUBLICATIONS

Schlüter, M., "Transesophageal Cross-Sectional Echocardiography with a Phased Array Transducer System", Apr. 1982, Br Heart F, vol. 48: 67–72.

Hisanaga, K. and A., "A New Trans-Digestive-Tract Scanner with a Gastro-Fiber Scope", Department of Internal Medicine, Mitsubishi Nagoya Hospital.

Primary Examiner—Francis Jaworski
Assistant Examiner—George Manuel

[57] ABSTRACT

An endoscope ultrasound probe for use with an ultrasound imaging system in transesophageal echo cardiography comprises a motorized positioning system which provides for automated control of an ultrasound transducer array. The positioning system employs an electric motor for rotating the array which is positioned in the distal end of the probe. A switch mechanism may be manipulated to provide power to actuate the motor. The motor is mechanically coupled to the array providing the capability to rotate the array to any angular position to provide a plurality of scan planes for obtaining a plurality of corresponding two-dimensional cross-sectional images. Further, the positioning system may comprise a position feedback mechanism coupled to the array for providing remote imaging system electronics with array position indications corresponding to each of a plurality of corresponding two-dimensional cross-sectional images. Also, the positioning system may be electronically controlled by a controller in the imaging system for providing three-dimensional images of a subject.

31 Claims, 4 Drawing Sheets

TRANSDUCER POSITIONING SYSTEM

BACKGROUND

Transesophageal echo cardiography is an established technique in the area of cardiac imaging and involves the insertion of an ultrasound probe into a subject's esophagus to scan the heart from inside the esophagus. An ultrasound probe may be formed by modifying a flexible endoscope, whereby an ultrasound transducer array is affixed to the distal end of the endoscope. Typically, the probe is used with an ultrasound imaging system having electronics for remote excitation of the array to obtain cross-sectional images of the heart along a variety of scan planes. An ultrasound probe having a rotatable array is described in U.S. Pat. No. 4,543,960 to Harui.

SUMMARY OF THE INVENTION

Manual control of transducer position has been suggested. However, a manual positioning system has numerous limitations, providing an imprecise means for positioning an endoscopic ultrasound transmitting device. For example, with a manual system the speed at which the array may be rotated is not readily controllable. As such, an operator manually controlling array rotation could induce stress on positioning system components as well as probe components by abruptly changing the rotational speed and/or direction. Further, a sufficiently abrupt change in rotational speed and/or direction could overtorque the aforementioned components leading to potentially serious damage to the probe.

Another problem with a manual positioning system is that the elasticity of the drive mechanism from the handle to the transducer may give a poor feel to the position control mechanism. As such, an operator may have difficulty correlating the extent of manipulation of the position mechanism required for precise control of the transducer position.

The present invention solves the aforementioned problems of the prior art through a unique positioning system employed in an endoscopic ultrasound probe. In accordance with one aspect of the present invention, the positioning system employs an electrically powered motor which is coupled to a flexible drive shaft for rotating a transducer array supported in the distal end of a probe. Unlike the prior art, the motor precisely controls the speed of array rotation which eliminates abrupt rotational speed variations, thereby minimizing potentially damaging overtorque situations. Also, the motor provides vernier action allowing for precise control over the position of the array without extensive hand motion. Further, the motorized positioning system may be integrated with remote ultrasound electronics for providing three-dimensional images of a subject.

In a preferred embodiment, the motor is positioned in a handle which is coupled to the distal end of the probe by the flexible drive shaft. Preferrably, the motor is a continuous direct current powered motor, though it may also be an alternating current motor or a stepper motor. Further, a switch mechanism may be manipulated to provide power to actuate the motor. The motor is mechanically coupled to the array, preferably by a plurality of gears, and provides the capability to rotate the array to any angular position to provide a plurality of scan planes for obtaining a plurality of corresponding two-dimensional cross-sectional images.

In accordance with another aspect of the invention, the positioning system minimizes the torque on the flexible drive shaft, thereby preventing an articulation tube which houses the drive shaft from twisting. The motor is coupled to the flexible drive shaft by the gears which provide gear reduction to minimize the torque in the drive shaft. Low torque in the drive shaft serves to prevent twisting of the articulation tube which, if twisted, would cause the probe tip to rotate such that its orientation would be lost.

In accordance with yet another aspect of the present invention, the positioning system comprises a position feedback mechanism coupled to the array for providing remote imaging electronics with array position data corresponding to each of a plurality of two-dimensional cross-sectional images. In a preferred embodiment, the position feedback mechanism comprises a potentiometer positioned in the handle. The potentiometer is mechanically coupled to the array by a plurality of gears such that the rotation of the array produces corresponding changes in the potentiometer output. Additionally, a drive mechanism is mechanically linked to the gears. As such, the motor drives the gears which rotate the array to provide a plurality of array positions for obtaining two-dimensional cross-sectional images. Since the potentiometer is also coupled to said gears, the rotation of the array produces corresponding changes in the potentiometer output. The potentiometer output is provided to the remote imaging electronics where it is transformed into an angular position of the array and displayed on a CRT display.

A motorized positioning system of the present invention allows for automated control of the array position via the imaging system electronics. As such, it is possible to precisely rotate the array to various positions to obtain corresponding two-dimensional cross-sectional images at desired points in a subject's electrocardiogram (ECG) cycle. Since three-dimensional imaging requires multiple two-dimensional cross-sectional images obtained at the same point in an ECG cycle, an imaging system having a motorized positioning system would be capable of producing three-dimensional images.

To that end, the motorized positioning system of the present invention is preferrably electronically controlled for providing three-dimensional images of a subject. A controller controls the power to actuate the motor for rotating the array. As the array is rotated, the controller may receive position data from the feedback mechanism.

During an ECG cycle, a subject's heart is constantly in motion such that, for a single array position, the imaging system obtains unique two-dimensional cross-sectional images for each time in the cycle. Accordingly, the controller may be sychronized to the subject's ECG cycle for obtaining image data at particular times in multiple cycles. In conjunction with the feedback positioning system, the controller periodically rotates the array to a plurality of positions to obtain image data along a plurality of corresponding scan planes. The image data is processed by the remote electronics to provide multiple two-dimensional cross-sectional images corresponding to the plurality of scan planes and associated with specific times in the ECG cycle. The two-dimensional cross-sectional images are subsequently combined to provide three-dimensional images of the subject's heart.

BRIEF DESCRIPTION OF THE DRAWINGS

In the enclosed drawings like reference characters refer to the same parts throughout the different views. The drawings are not necessarily to scale, emphasis instead being placed upon illustrating the principles of the invention.

DETAILED DESCRIPTION

Figure 1:
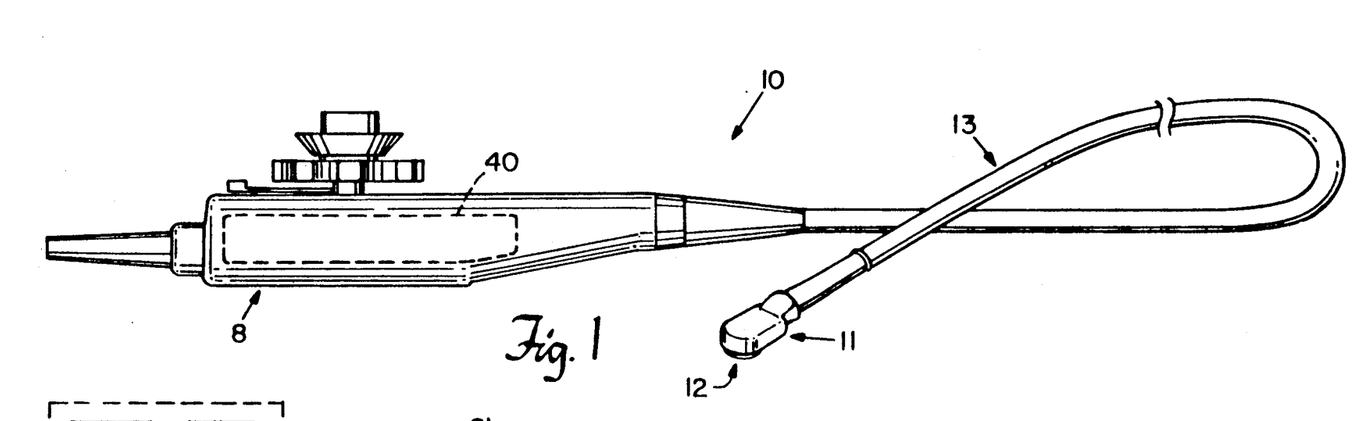
FIG. 1 provides a perspective view of an endoscopic ultrasound probe in accordance with the present invention.

An endoscopic ultrasound probe illustrating the principles of the present invention is shown in FIG. 1. A probe 10 is formed by modifying an endoscope whereby a rotatable ultrasound transducer array 12 is positioned in a probe tip housing 11 located at its distal end. The array 12 obtains image data along a scan plane which is perpendicular to a plane of the array face and corresponds to the angular position of the array. In a preferred embodiment, a positioning system 40 for rotating the array is located in a handle 8 and is mechanically coupled to the array via a flexible drive shaft 24. The positioning system is capable of rotating the array to various angular positions to obtain image data along a plurality of corresponding scan planes. The array is coupled to remote electronics of an ultrasound imaging system by the articulating tube 13, providing image data to the remote electronics which produces a plurality of two-dimensional cross-sectional images corresponding to the scan planes.

Figure 2:
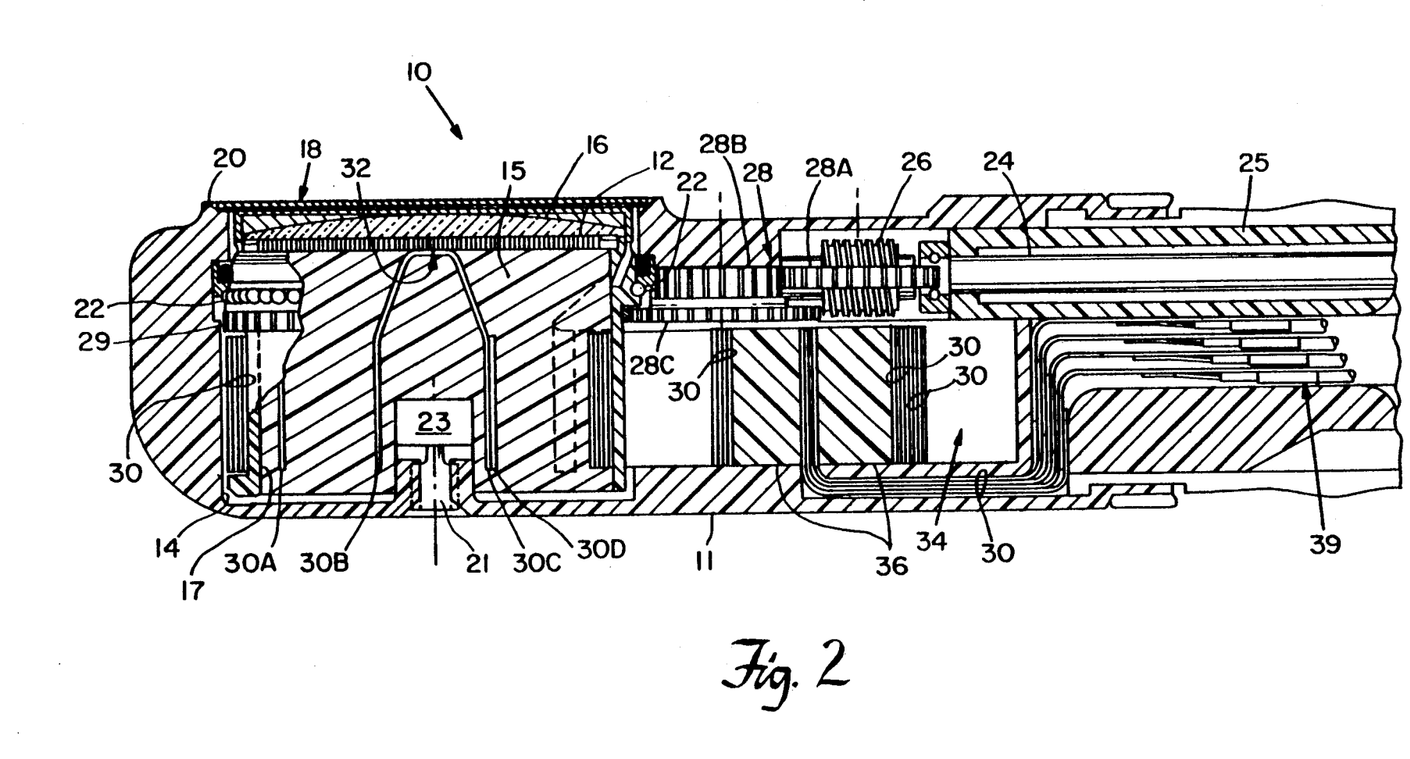
FIG. 2 is a longitudinal cross-sectional view of a portion of an endoscopic ultrasound probe.

A longitudinal cross-sectional view of the distal end of the ultrasound probe is shown in FIG. 2. The probe 10 has a probe housing 11 at its distal end shaped for insertion into a subject's esophagus. The rotatable ultrasound transducer array 12 comprises a plurality of elongated piezoelectric transducer elements arranged in a plane. The array is positioned on a support structure 17 within an inner volume 14 located in the probe housing 11 at the distal end of the probe.

A compound lens assembly 16 covering the rotatable array 12 serves to focus the energy emitted by the array along a plane which is parallel to the array elements. Additionally, this energy emitted from the array is electronically focused in a scan plane which perpendicular to the plane of the array elements. A stationary cover assembly 18 is mounted over the inner housing 11 above the array. The cover prevents undesireable substances from touching the lens. A layer of grease 20 is located between the lens assembly 16 and the cover 18 and serves as a transmission medium.

The array is electrically connected to a flexible cable assembly 30 for providing image data to the remote ultrasound imaging electronics. The flexible cable assembly extends from the array, through the inner volume 14 and a rear volume 34, to a plurality of individual conductors 39 adjacent to the rear volume which are coupled to the remote ultrasound electronics via cable 25. In one embodiment, the flexible cable assembly is a single flex cable comprising a plurality of individual flex cable extensions 30A-D, each having a plurality of signal lines printed thereon. A mass of acoustical damping material 15 fills the volume within support structure 17, encapsulating a portion of the individual flex cables. The acoustical damping material 15 absorbs acoustic signals from the back of the array.

The array 12 is capable of being rotated about an axis extending through the center of the array and a shaft 21 for obtaining cross-sectional images along a variety of scan planes. The array is coupled to the rotatable support structure which is mechanically linked to a plurality of ball bearings 22 and to a bearing 23 at the shaft. Rotation of the array is achieved by employing a positioning means, such as the positioning system of the present invention as described below, for manipulating the rotating flexible drive shaft 24, which is coupled to a worm gear 26. More specifically, the rotating cable 24, resembling a speedometer cable, is mechanically linked to the worm gear 26. The rotation of the flexible drive shaft 24 causes the worm gear 26 to rotate about a common shaft. The worm gear is mechanically linked to a first gear 28A such that rotation of the worm gear causes the first gear to rotate about an axis which is parallel to the axis of rotation for the array. The first gear 28A is one of a plurality of gears 28 which are mechanically linked to each other and have parallel axes of rotation. Thus, the rotation of the worm gear drives the first gear 28A, the rotation of first gear drives the second gear 28B, the rotation of the second gear drives the third gear 28C. The third gear is mechanically linked to a ring gear 29 which is coupled to the support structure 17. Thus, the rotation of the third gear causes the ring gear to turn such that the array rotates.

Figure 3:
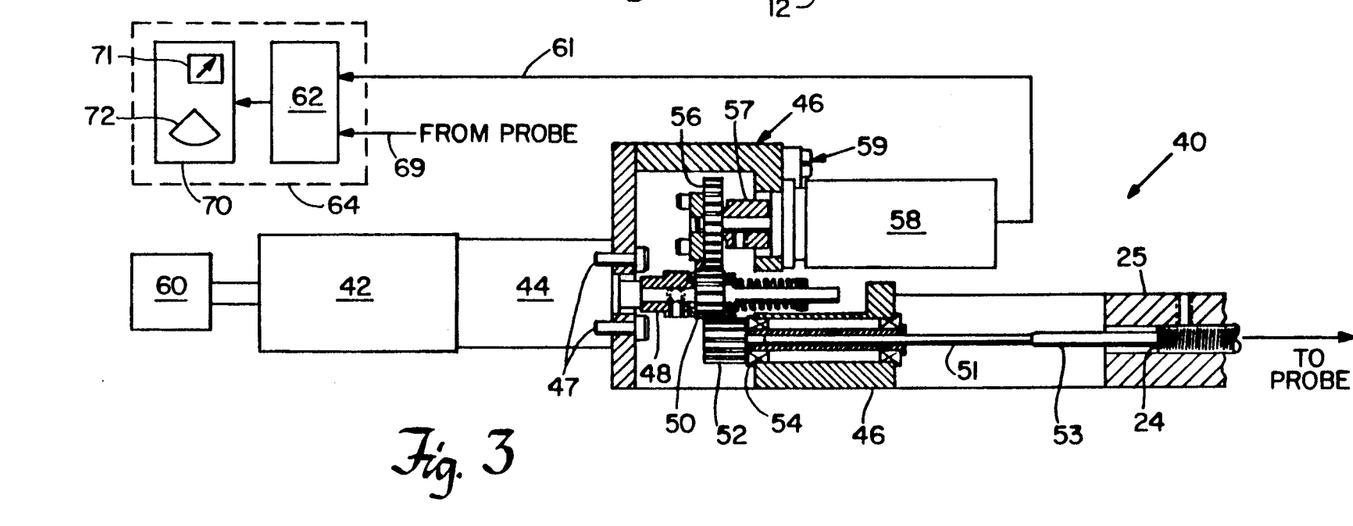
FIG. 3 is a cross-sectional view of a positioning system of the present invention.

In accordance with the present invention, a positioning system for rotating the array is shown in FIG. 3. The positioning system 40 employs an electrically powered motor 42 to rotate the array. In a preferred embodiment, the motor is positioned in the handle 8, although it may be located in the probe tip housing 11 without departing from the scope of this invention. However, with the motor in the handle in accordance with a preferred embodiment, the size of the probe tip housing 11 can be minimized. Preferably, the motor 42 is a direct current (DC) powered motor, such as a DC servo motor. Alternatively, the motor may be an alternating current (AC) powered motor or a stepper motor. A gearbox 44 is integrally coupled to the motor for reducing the rotational speed of the motor. The motor/gearbox assembly is mounted to a housing 46 by screws 47.

The motor 42 is mechanically coupled to the array, providing the capability to rotate the array to any angular position for obtaining image data along a plurality of scan planes. More specifically, the motor is mechanically linked to a plurality of gears (50, 52 and 56) which are coupled to the rotating flexible drive shaft 24. To rotate the array, the motor is actuated by a manipulating a switch mechanism 60 which is described in detail below. The motor is mechanically coupled to a first gear 50 by a shaft 48. Thus, the motor turns the shaft which rotates the first gear. A second gear 52 is mechanically linked to the first gear 50, so the rotation of the first gear drives the second gear. A second shaft 51 is supported on a plurality of bearings 54 and is attached to a rotating shaft 53 of the rotating cable 24. Since the second shaft is integrally coupled to the second gear 52, the rotation of the second gear drives the two shafts 51 and 53. The rotating shaft 51 drives the rotating cable 24 causing the array to rotate to a plurality of positions. For each angular position, the array provides image data corresponding to a two-dimensional cross-sectional image via line 69 to remote imaging electronics 64.

In accordance with another feature of the present invention, the positioning system comprises a position feedback mechanism 58 capable of providing the remote imaging electronics with precise angular position data of the array which corresponds to the scan plane associated with a two-dimensional cross-sectional image. In a preferred embodiment, shown in FIG. 3, the position feedback mechanism 58 comprises a potentiometer mounted to the housing 46 in the handle 8. Alternatively, the position feedback mechanism may comprise a digital or analog optical encoder. Also, the position feedback mechanism may be located in the probe tip housing 11 without departing from the scope of this invention. However, with the position feedback mechanism in the handle, the size of the probe tip housing 11 can be minimized.

To provide precise angular position data of the array, the potentiometer is coupled to the array such that rotation of the array produces corresponding changes in the potentiometer output. More specifically, the potentiometer 58 is mechanically coupled to the array via the plurality of gears (50, 52 and 56). The potentiometer 58, like the motor 42, has a rotatable shaft 57 which controls the potentiometer output. The rotatable shaft 57 is coupled to a third gear 56 which is mechanically linked to the second gear 52 by the first gear 50. To rotate the array, the motor 42 causes the first gear to rotate which drives the second gear 52 (for rotating the array) as well as the third gear 56. Since the rotation of the third gear 56 turns the rotatable shaft 57, the potentiometer output changes in conjunction with the rotatation of the array. It should be noted that, although the feedback provided by the potentiometer would be helpful in a manual positioning system, it has particular utility in an electronic motor driven system.

The potentiometer output may be transformed into an angular position of the array and displayed on a CRT display 70 in remote imaging electronics. To accomplish this, the potentiometer output is sent to the controller 62 located in the remote imaging electronics 64 via line 61. The controller transforms the potentiometer output to an angular position corresponding to an array orientation by employing appropriate electronics and software. The angular position is sent to the CRT display 70 and displayed on an angular position display window 71 which is located adjacent to a main two-dimensional image window 72.

Figure 4A:
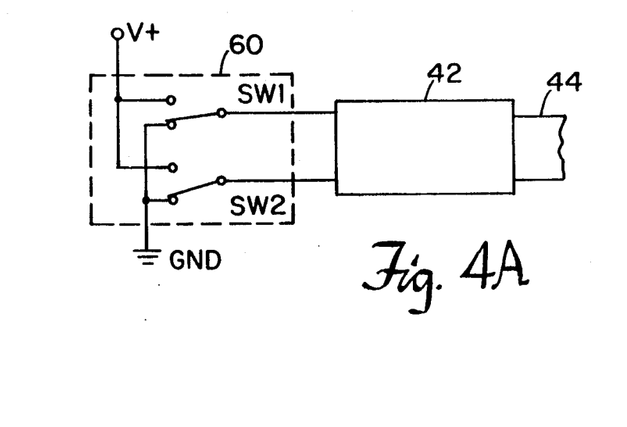
FIG. 4A shows a schematic representation of switch mechanism for use with the positioning system of FIG. 3.

In one embodiment, the positioning system 40 is directly controlled by a switch mechanism 60, as shown in FIG. 4A. More specifically, the switch mechanism 60 controls the input power to the motor, as well as its polarity, for actuating the motor 42 which causes the array to rotate in a clockwise or counter-clockwise direction. The switch mechanism comprises a pair of two-position switches SW1 and SW2 which may be located on the endoscope handle 8 or in the ultrasound imaging system. Alternatively, the switch mechanism 60 may comprise one three-position switch without departing from the scope of the invention. The switch mechanism may comprise mechanically activated switches, relays or semiconductor switches without departing from the scope of this invention.

Referring to FIG. 4A, the remote electronics provides to the switches a power source represented by a voltage source V+ and a ground GND. Accordingly, each switch has a first position corresponding to GND and a second position corresponding to V+. The switches may be positioned to inhibit power to the motor or to provide power corresponding to one of two opposite polarities. For example, both switches are normally set to the same postion such that the motor receives no power and the array remains stationary. However, when the switch SW1 is set to V+ with the switch SW2 set to GND, the motor causes the array to rotate in a first direction. Alternatively, when the switch SW2 is set to V+ and the switch SW1 is set to GND, the motor causes the array to rotate in a the opposite direction.

Figure 4B:
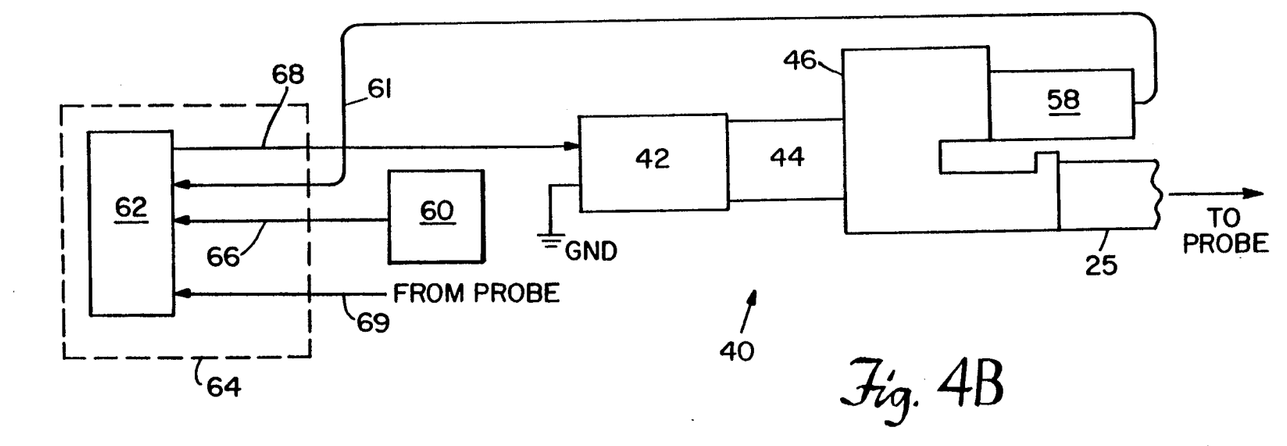
FIG. 4B illustrates an electronically controlled positioning system for use with an endoscopic probe in obtaining three-dimensional images of a subject.

In accordance with another feature of the present invention, the positioning system 40 may be employed in an ultrasound imaging system capable of providing three-dimensional images of a subject. Referring to FIG. 4B, a controller 62 is located in remote imaging electronics 64 and is coupled to the positioning system 40. More specifically, the controller is coupled to the motor 42 via line 68 and provides power to actuate the motor 42. As such, the controller controls the rotation of the array. Further, the position feedback mechanism 58 is coupled to the controller via line 61, providing precise angular position data (which corresponds to the scan plane orientation) as the array is rotated through a plurality of scan planes. Preferrably, the controller correlates the array position data with the power provided to actuate the motor such that the array is rotated to obtain image data at regularly incremented angular positions.

During an ECG cycle, a subject's heart is constantly in motion such that the imaging system obtains unique two-dimensional cross-sectional images at each time in the cycle for a single array position. Accordingly, the controller 62 may sychronized to the subject's ECG cycle for obtaining image data at particular times ($S_x$) in multiple cycles. To accomplish this, the switch mechanism 60 is manipulated to provide a signal via line 66 to the controller to initiate the three-dimensional imaging process. The controller, in conjunction with the position feedback mechanism, subsequently rotates the array to a plurality of regularly incremented angular positions ($P_x$) to obtain image data along a plurality of corresponding scan planes. The image data is processed by the remote electronics 64 to provide multiple two-dimensional cross-sectional images corresponding to the plurality of regularly incremented scan planes and associated with the specific times in the ECG cycle. The two-dimensional cross-sectional images are subsequently combined to provide three-dimensional images of the subject's heart.

Figure 5A:
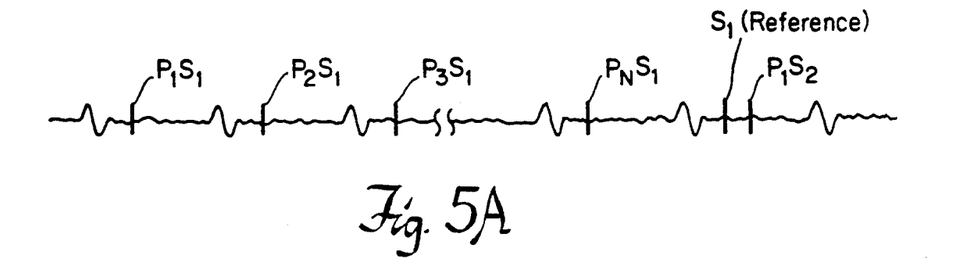
FIG. 5A is a graphical representation of multiple electrocardiogram cycles in which a particular time is indicated in each cycle.

Referring to FIG. 5A, the system may be configured to obtain a single three-dimensional image corresponding to a specific time in a subject's ECG cycle. To that end, the controller is synchronized to obtain image data at a desired time ($S_1$) in a plurality of cycles. With the array having an initial angular position ($P_1$), the controller obtains image data from the array in a first cycle at the time $S_1$. The controller rotates the array to a plurality of angular positions to obtain image data along a plurality of corresponding scan planes at the time $S_1$ in subsequent ECG cycles. The image data is processed to produce two-dimensional cross-sectional images that are combined to provide a three-dimensional image of the subject's heart at the desired time $S_1$ of the subject's ECG cycle.

Figure 5B:
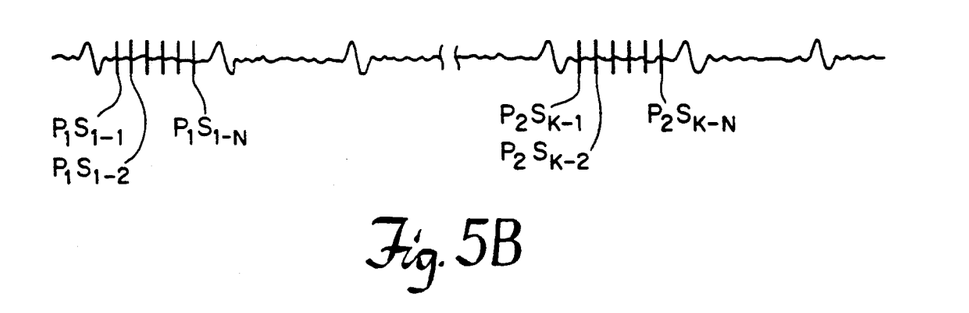
FIG. 5B is a graphical representation of multiple electrocardiogram cycles in which a plurality of particular times are indicated in various cycles.

The imaging system employing the present invention may also be employed to provide multiple three-dimensional images of the subject corresponding to a plurality of times ($S_x$) in the subject's ECG cycle. Referring to FIG. 5B, the controller is programmed to obtain image data at particular times ($S_1, S_2, \ldots S_N$) in multiple ECG cycles. Assuming the array has an initial position ($P_1$), the controller obtains image data at the times ($S_1, S_2, \ldots S_N$) in a first ECG cycle. The controller then utilizes the position feedback mechanism to rotate the array to a second angular position P2 to obtain image data at the particular times ($S_1, S_2, \ldots S_N$). The process is repeated until the controller has rotated the array to a plurality of scan positions and obtained image data at the aforementioned times in subsequent ECG cycles. The image data is processed to provide multiple two-dimensional cross-sectional images that are combined to provide multiple three-dimensional images of the subject's heart corresponding to the times ($S_1, S_2, \ldots S_N$) of the subject's ECG cycle.

While this invention has been particularly shown and described above with references to specific embodiments, the foregoing and other changes in form and detail may be made by one skilled in the art without departing from the spirit and scope of the invention.

We claim:

1. A endoscopic ultrasound probe for use with a remote ultrasound imaging system comprising:
    a substantially planar rotatable transducer array within the distal end of said probe having a scan plane perpendicular to a plane of the array for obtaining a corresponding two-dimensional cross-sectional image relative to each position of the array;
    a cable for connecting the array with remote ultrasound imaging system electronics; and
    a positioning system which comprises an electrically powered motor for rotating the array about an axis perpendicular to said plane of the array to provide a plurality of scan planes for obtaining a plurality of corresponding two-dimensional cross-sectional images.

2. An endoscopic ultrasound probe as claimed in claim 1 further comprising a position feedback mechanism coupled to the array for providing the ultrasound imaging system electronics with array angular position data corresponding to each of the plurality of two-dimensional cross-sectional images.

3. An endoscopic ultrasound probe as claimed in claim 1 further comprising a switch mechanism which is manipulated for providing electrical power to the motor.

4. An endoscopic ultrasound probe as claimed in claim 3 in which the switch mechanism is coupled to a controller positioned in the remote ultrasound imaging system electronics wherein manipulating the switch causes the controller to provide electrical power to the motor.

5. An endoscopic ultrasound probe as claimed in claim 1 wherein the motor is a direct current powered motor.

6. An endoscopic ultrasound probe as claimed in claim 1 further comprising a controller synchronized to a particular time in a subject's electrocardiogram cycle and coupled to the motor, wherein the controller periodically actuates the motor to rotate the array to various orientations which provides the plurality of scan planes for obtaining the plurality of corresponding two-dimensional cross-sectional images at the particular time in the subject's electrocardiogram cycle for providing a three-dimensional image associated with that particular time.

7. An endoscopic ultrasound probe as claimed in claim 1 further comprising a handle coupled to the cable and housing the motor.

8. An endoscopic ultrasound probe as claimed in claim 1 further comprising:
    a flexible drive shaft for rotating the array; and
    a plurality of gears mechanically coupling the motor to the flexible drive shaft wherein the gears provide low torque on the flexible drive shaft.

9. An endoscopic ultrasound probe for use with remote ultrasound imaging electronics in transesophageal echo cardiography comprising:
    a substantially planar rotatable transducer array within the distal end of said probe having a scan plane which is perpendicular to a plane of the array and which corresponds to a position of the array;
    a cable for connecting the array with the remote ultrasound imaging electronics;
    a drive mechanism for rotating the array about an axis perpendicular to said plane of the array to provide a plurality of positions corresponding to a plurality of scan planes for obtaining a corresponding plurality of two-dimensional cross-sectional images; and
    a position feedback mechanism coupled to the array for providing the ultrasound imaging electronics with array position data corresponding the plurality of positions of the array associated with the corresponding plurality of two-dimensional cross-sectional images.

10. An endoscopic ultrasound probe as claimed in claim 9 wherein the position feedback mechanism comprises a potentiometer.

11. An endoscopic ultrasound probe as claimed in claim 9 further comprising a handle wherein the position feedback mechanism is positioned in the handle.

12. An endoscopic ultrasound probe as claimed in claim 10 further comprising a controller which is synchronized to a subject's electrocardiogram cycle and which is coupled to the drive mechanism for actuating rotation of the array, wherein the controller periodically actuates the drive mechanism to rotate the array to a achieve a plurality of particular scan planes for obtaining a corresponding plurality of two-dimensional cross-sectional images at a specific time in the subject's electrocardiogram cycle, wherein the controller coordinates the array position data along with the corresponding two-dimensional cross-sectional images to construct a three-dimensional image of the subject associated with that particular time.

13. An endoscopic ultrasound probe as claimed in claim 9 further comprising a display coupled to the position feedback mechanism for displaying the plurality of positions of the array.

14. An endoscopic ultrasound probe as claimed in claim 10 further comprising a plurality of gears mechanically coupling the position feedback mechanism and the array.

15. An endoscopic ultrasound probe as claimed in claim 10 wherein the drive mechanism comprises an electrically powered motor.

16. An endoscopic ultrasound probe as claimed in claim 9 further comprising:
  a flexible drive shaft for rotating the array; and
  a plurality of gears mechanically coupling the motor to the flexible drive shaft wherein the gears provide low torque on the flexible drive shaft.

17. An ultrasound imaging system comprising:
  a transesophageal ultrasound probe comprised of a rotatable transducer array having a plurality of transducer elements arranged in a plane, the array having a scan plane perpendicular to the plane of the transducer elements and corresponding to an angular position of the array;
  an electric motor for rotating the array to achieve a plurality of angular positions;
  a position feedback mechanism coupled to the array capable of providing array position data corresponding to the plurality of angular positions; and
  ultrasound imaging electronics coupled to the probe by a flexible drive shaft and comprising a controller which is synchronized to a particular time in a subject's electrocardiogram cycle, the controller being coupled to the motor for actuating rotation of the array and being coupled to the position feedback mechanism for recieving the array position data in response to rotation of the array, wherein the controller periodically actuates the motor to rotate the array to achieve a plurality of angular positions for obtaining two-dimensional images along a corresponding plurality of scan planes at the particular time in the subject's electrocardiogram cycle and wherein controller correlates the obtained two-dimensional images along with the position data received from the position feedback mechanism in constructing a three-dimensional image associated with that particular time.

18. An ultrasound imaging system as claimed in claim 17 wherein the imaging electronics further comprises a display coupled to the position feedback mechanism for displaying plurality of angular positions of the array.

19. An ultrasound imaging system as claimed in claim 17 wherein the motor is electrically powered.

20. An ultrasound imaging system as claimed in claim 17 wherein the positioning feedback mechanism comprises a potentiometer.

21. An ultrasound imaging system as claimed in claim 17 in which the controller is further synchronized to a plurality of particular times in a subject's electrocardiogram cycle, wherein the controller periodically actuates the motor to rotate the array to achieve a plurality of angular positions for obtaining two-dimensional images along a corresponding plurality of scan planes at the plurality of particular times in the subject's electrocardiogram cycle and wherein controller correlates the two-dimensional images along with the position data received from the position feedback mechanism for each of the particular times in constructing three-dimensional images associated with the plurality of particular times.

22. An endoscopic ultrasound probe as claimed in claim 17 further comprising:
  a flexible drive shaft for rotating the array; and
  a plurality of gears mechanically coupling the motor to the flexible drive shaft wherein the gears provide low torque on the flexible drive shaft.

23. A method for rotating a transducer array supported in an endoscopic ultrasound probe comprising:
  providing a rotatable substantially planar transducer array within the distal end of said probe having a scan plane perpendicular to a plane of the array, ultrasound imaging electronics for producing a two-dimensional cross-sectional image corresponding to a particular scan plane and an electrically powered motor mechanically coupled to the array by a flexible drive shaft; and
  actuating the motor to rotate the array about an axis perpendicular to said plane of the array for providing a plurality of scan planes for obtaining a plurality of corresponding two-dimensional cross-sectional images.

24. A method as claimed in claim 23 further comprising manipulating a switch for providing electrical power to acutate the motor.

25. A method as claimed in claim 23 further comprising monitoring the rotation of the array with a position feedback mechanism to provide the remote ultrasound imaging electronics with array angular position indications corresponding to each of the two-dimensional cross-sectional images.

26. A method as claimed in claim 25 further comprising displaying the angular position indications of the array on a display.

27. A method for rotating a transducer array supported in an endoscopic ultrasound probe comprising:
  providing a rotatable substantially planar transducer array within the distal end of said probe having a scan plane perpendicular to a plane of the array and which corresponds to a position of the array, remote ultrasound imaging electronics for producing a two-dimensional cross-sectional image corresponding to a particular scan plane of the array, a motor coupled to the array by a flexible drive shaft and a position feedback mechanism coupled to the array;
  actuating the motor for rotating the array about an axis perpendicular to said plane of the array to a plurality of positions to provide a plurality of corresponding scan planes for obtaining a plurality of corresponding two-dimensional cross-sectional images; and
  monitoring the plurality of positions via the position feedback mechanism for providing the remote ultrasound imaging electronics with position data corresponding to each of the two-dimensional cross-sectional images.

28. In an ultrasound imaging system, a method for obtaining a three-dimensional image of a subject comprising:
  providing a transesophageal ultrasound probe comprising a rotatable substantially planar transducer array within the distal end of said probe having a scan plane perpendicular to a plane of the array and corresponding to a position of the array, a motor for rotating the array, a controller for actuating the motor and synchronized to the subject's electrocardiogram cycle, and ultrasound imaging electronics coupled to the probe for producing a two-dimensional cross-sectional image corresponding to a particular scan plane of the array, and a position feedback mechanism coupled to the array for providing array position indications;

directing the array to a first orientation to provide the corresponding scan plane for producing the corresponding two-dimensional cross-sectional image;

actuating the motor via the controller to rotate the array about an axis perpendicular to said plane of the array to subsequent orientations to provide the corresponding scan planes for producing the corresponding two-dimensional cross-sectional images, wherein each image is associated with a particular time in the subject's electrocardiogram cycle;

monitoring the array positions via the position feedback mechanism for providing the remote ultrasound imaging electronics with position indications corresponding to each of the two-dimensional cross-sectional images; and processing the two-dimensional cross-sectional images along with the position indications in the ultrasound imaging electronics to obtain a three-dimensional image associated with the particular time in the subject's electrocardiogram cycle.

29. A method as claimed in claim 28 further comprising displaying the position indications of the array on a display.

30. A method as claimed in claim 28 further comprising:

directing the array to a first orientation to provide the corresponding scan plane for producing a plurality of corresponding two-dimensional cross-sectional images, each image being associated with a particular time in the subject's electrocardiogram cycle;

actuating the motor via the controller to rotate the array to subsequent orientations to provide the corresponding scan planes for producing a plurality of corresponding two-dimensional cross-sectional images, each image being associated with said particular time in the subject's electrocardiogram cycle;

monitoring the array positions via the position feedback mechanism for providing the remote ultrasound imaging electronics with position indications corresponding to the two-dimensional cross-sectional images; and processing the two-dimensional cross-sectional images along with the position indications in the ultrasound imaging electronics to obtain three-dimensional images associated with the particular times in the subject's electrocardiogram cycle.

31. A method as claimed in claim 28 further comprising displaying the position indications of the array on a display.

* * * * *